(12) United States Patent
Tanaka et al.

(10) Patent No.: US 7,736,001 B2
(45) Date of Patent: Jun. 15, 2010

(54) FOCUSING UNIT AND OPHTHALMIC PHOTOGRAPHING APPARATUS

(75) Inventors: Shinya Tanaka, Tokyo (JP); Tomoyuki Iwanaga, Yokohama (JP); Hiroshi Itoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/945,793

(22) Filed: Nov. 27, 2007

(65) Prior Publication Data

US 2008/0123050 A1 May 29, 2008

(30) Foreign Application Priority Data

Nov. 29, 2006 (JP) .............................. 2006-321633

(51) Int. Cl.
*A61B 3/10* (2006.01)
*A61B 3/14* (2006.01)

(52) U.S. Cl. ........................ 351/214; 351/206; 351/221

(58) Field of Classification Search .................. 351/206, 351/214, 221
See application file for complete search history.

(56) References Cited

U.S. PATENT DOCUMENTS 5,371,557 A 12/1994 Nanjho
5,382,988 A 1/1995 Nanjho
5,713,047 A * 1/1998 Kohayakawa ................. 396/18
6,304,723 B1 10/2001 Kohayakawa
7,360,895 B2 * 4/2008 Cornsweet et al. .......... 351/206
2003/0025876 A1 * 2/2003 Nanjo ......................... 351/206
2006/0077346 A1 * 4/2006 Matsumoto ................. 351/214
2008/0024860 A1 * 1/2008 Yaroslavsky et al. ........ 359/372

FOREIGN PATENT DOCUMENTS

| JP | 5-95902 | 4/1993 |
| JP | 6-142050 | 5/1994 |
| JP | 2005-245894 | 9/2005 |
| JP | 2007-143671 | 6/2007 |

* cited by examiner

*Primary Examiner*—Jessica T Stultz
*Assistant Examiner*—Mahidere S Sahle
(74) *Attorney, Agent, or Firm*—Canon USA Inc IP Div (57) ABSTRACT

A focusing unit can be inserted into and removed from an illumination light path by rotating around a supporting portion. An index light source, a green LED, is attached to the bottom of a base. A transparent acrylic-resin disk is fixed to the base. A deflection prism is attached to the bottom of the disk. A beam from the light source enters the deflection prism. A focus index forming portion is provided on the top of the disk. In the center of a light-shielding portion is formed a slit-like opening, under which split prisms are provided. Deflected by the prisms, the beam from the light source is split into two, right-half and left-half, directional beams, and combined with an illumination optical system, in the form of two slit images, at the opening.

3 Claims, 7 Drawing Sheets

FOCUSING UNIT AND OPHTHALMIC PHOTOGRAPHING APPARATUS

BACKGROUND OF THE INVENTION

1. Field of the Invention

The present invention relates to an ophthalmic photographing apparatus used in opthalmologist's offices, clinics, and so forth.

2. Description of the Related Art

A fundus camera disclosed in Japanese Patent Laid-Open No. 5-95902 includes an index for focus indication, a light source that illuminates this index, and a projection optical system that has a split prism for projecting index images onto the fundus of a subject's eye from different positions of the pupil.

In addition, there is also known a method such that a minute prism is provided in an illumination optical system, a slit image illuminated by fundus observation light is projected onto the fundus of an eye, and focus adjustment is performed as disclosed in Japanese Patent Laid-Open No. 6-142050.

In the case of the above-described method, since both a focus index projection lens barrel and a minute mirror that branch from the illumination optical system must be moved in the optical axis direction, a large space is necessary.

In the case of the method in which a minute prism is provided in an illumination optical system, since fundus illumination light is decentered by a prism to project a focus index, the focus index is darker than the surrounding fundus region.

U.S. Pat. Appl. Pub. No. 2006/0077346 proposes an ophthalmic apparatus to solve the above problems, that is, the difficulty of downsizing the apparatus, the problem of increase in cost due to the number of components, adjustment, and so forth, and the problem of light quantity of the focus index. However, in the ophthalmic apparatus of U.S. Pat. Appl. Pub. No. 2006/0077346, a wavelength range different from that of the light illuminating the fundus must be used as an index light source. Specifically, it is necessary to use a near-infrared observation light source and an index light source whose wavelength regions are different from that of a white photographing light source for color photographing. Therefore, the art of U.S. Pat. Appl. Pub. No. 2006/0077346 is limited to non-mydriatic fundus cameras. In addition, the optical axis of the light source for focusing cannot be changed. Therefore, an opening is necessary in the center of a crystalline lens diaphragm, and ghost light can be generated.

As described above, in the conventional arts, the size of the apparatus can be increased or ghost light can be generated.

SUMMARY OF THE INVENTION

The present invention provides a focusing unit, and an ophthalmic photographing apparatus capable of inserting and removing a focusing unit into and from an illumination light path and easily projecting an index onto a fundus.

In an aspect of the present invention, a focusing unit for conjugating a fundus image of a subject's eye with a detecting surface of an image pickup element in a photographing optical system includes a light source to provide light of a given color for focusing the fundus image, a first optical member that deflects the light emitted by the light source, and a second optical member that splits the light deflected by the first optical member into one or more pairs of rays which travel along the optical axis spaced apart from one another in a direction perpendicular to the optical axis.

In another aspect of the present invention, an ophthalmic photographing apparatus includes a focus lens for focusing, a photographing optical unit having an image pickup element that converts an optical image incident through the focus lens into an electric signal, an illumination optical unit having a first illuminating member for illuminating a subject's eye, a separating unit configured to separate a light path of the photographing optical unit from a light path of the illumination optical unit, a second illuminating member, a deflection prism that deflects a light beam from the second illuminating member, and an opening that forms the light beam deflected by the deflection prism into a focus index and that is conjugate with a detecting surface of the image pickup element. The direction of the principal axis of the second illuminating member is different from the direction of the principal axis of the illumination optical unit.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Embodiments of the present invention will now be described with reference to the drawings.

Figure 1:
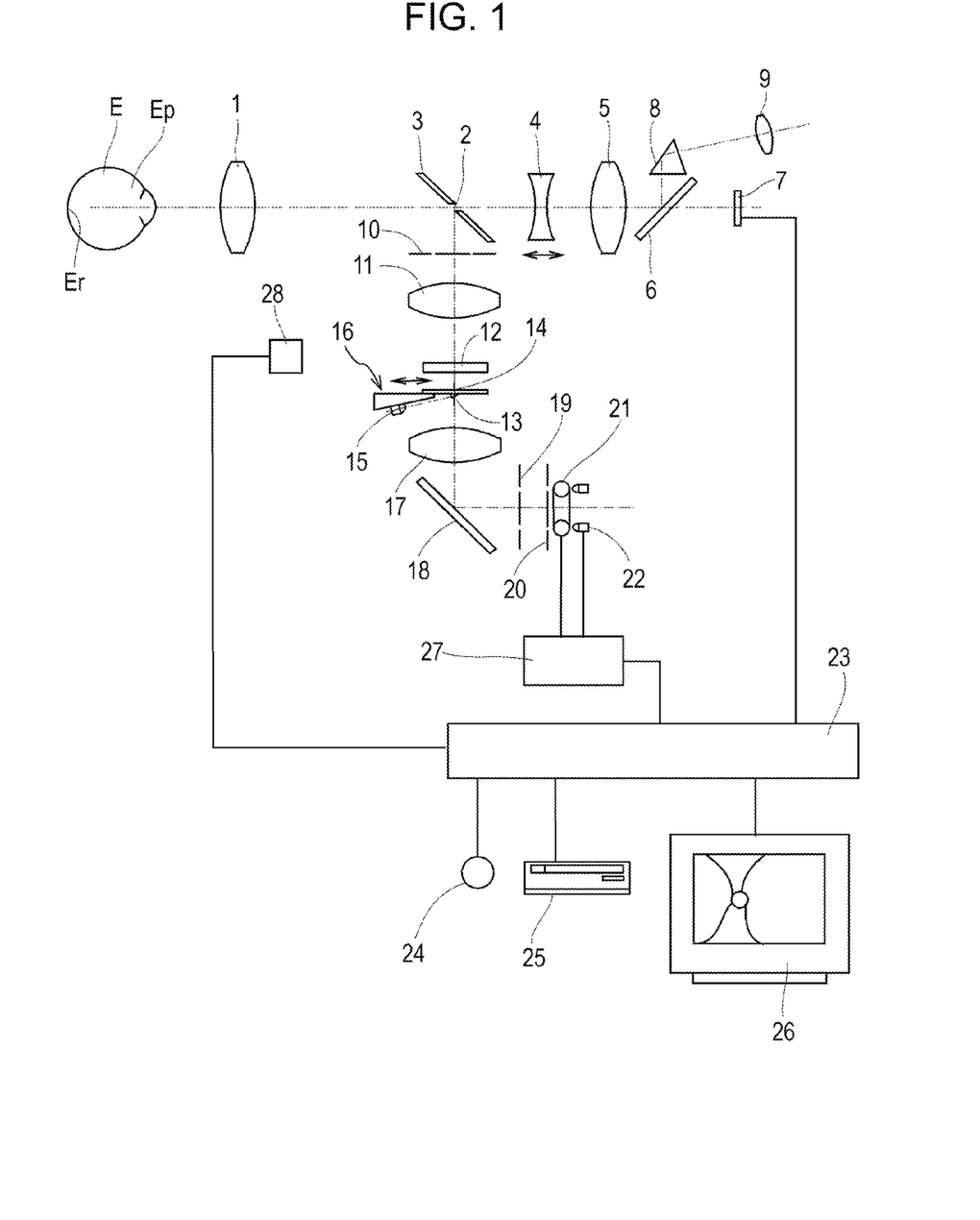
FIG. 1 shows the structure of a fundus camera.

FIG. 1 shows the structure of a fundus camera. An objective lens 1, an apertured mirror 3 having a photographing aperture 2, a focus lens 4 for focusing, a photographing lens 5, and a quick return mirror 6 are disposed in front of a subject's eye E. An image pickup element 7 converts an optical image incident through the apertured mirror 3, the focus lens 4, the photographing lens 5, and the quick return mirror 6 into an electrical image signal. The focus lens 4, the photographing lens 5, the quick return mirror 6, and the image pickup element 7 constitute a photographing optical system. In the reflection direction of the quick return mirror 6 are arranged a reflection prism 8 and an ocular lens 9, which constitute an observation optical system.

An illumination optical system illuminating the fundus of the subject's eye E has a cornea diaphragm 10 for restricting below-described illumination light, light beams of white LEDs 22, from the apertured mirror 3 to the vicinity of the cornea so that cornea reflection light does not enter the image pickup element 7. The illumination optical system has a first relay lens 11 and a black dot plate 12 that removes reflection due to the objective lens 1, which are arranged in sequence. Behind the black dot plate 12 is disposed a focusing unit 16, which comprises a deflection prism 13, a focus index forming portion 14, and an index illuminating member 15 for forming an index. The deflection prism, focus index forming portion and index illuminating member are integrated. The focusing unit 16 can be inserted into and removed from an illumination light path. This focusing unit 16 moves in the optical axis direction in conjunction with the movement of the focus lens 4 and can be removed from the light path when a still image is photographed.

The apertured mirror 3 is an optical member that separates a light path of the photographing optical system and a light path of the illumination optical system for illuminating the subject's eye E.

Behind the focusing unit 16 are disposed a second relay lens 17 and a mirror 18. In the reflection direction of the mirror 18 are arranged in sequence a crystalline lens diaphragm 19 that projects light beams onto the vicinity of the rear surface of the crystalline lens of the subject's eye E, a diaphragm 20 that projects light beams of below-described white LEDs onto the vicinity of the pupil Ep of the subject's eye E, a photographing illuminating member 21, and an observation illuminating member 22. The crystalline lens diaphragm 19 and the diaphragm 20 each have a ring-shaped opening.

Figure 2:
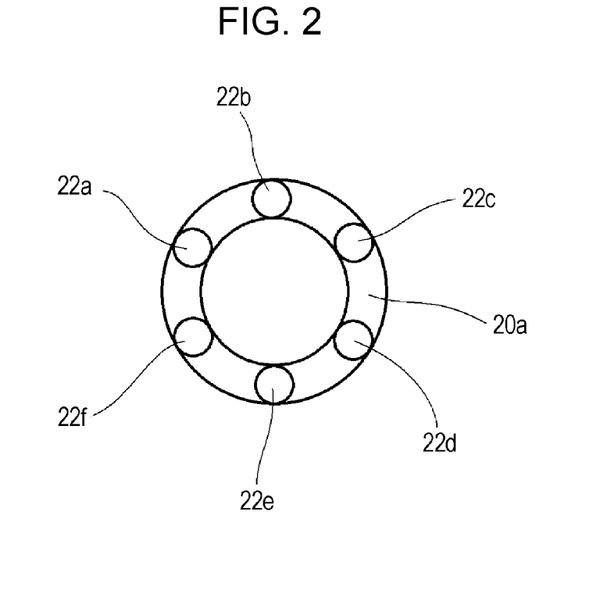
FIG. 2 illustrates the arrangement of a ring-shaped opening and an illumination light source.

As shown in FIG. 2, the observation illuminating member 22 includes six white LEDs 22a to 22f circularly arranged in the ring-shaped opening 20a of the diaphragm 20. The photographing aperture 2 in the apertured mirror 3 is substantially at a focal position of the first relay lens 11. The diaphragm 20 is disposed substantially at a focal position of the second relay lens 17.

A fundus image output from the image pickup element 7 is input into a control unit 23. The control unit 23 is connected to a photographing switch 24, a storage unit 25, and a monitor 26. In addition, the control unit 23 is connected to a light source driving circuit 27 that drives the photographing illuminating member 21 and the observation illuminating member 22, and a focusing unit driving unit 28 that inserts and removes the focusing unit 16 into and from the light path. The focusing unit driving unit 28 moves the focusing unit 16 in the optical axis direction in conjunction with the movement of the focus lens 4.

When photographing with this fundus camera, a photographer makes a person to be photographed sit in front of the fundus camera, observes the fundus Er of the subject's eye E through the ocular lens 9, and performs alignment of the subject's eye E with the fundus camera and focusing. Light beams emitted from the white LEDs 22a to 22f of the observation illuminating member 22 pass through the ring-shaped opening 20a of the diaphragm 20 and the ring-shaped opening of the diaphragm 19 and fall on the mirror 18. The light reflected by the mirror 18 passes through the second relay lens 17, the focusing unit 16, the black dot plate 12, the first relay lens 11, and the opening of the diaphragm 10 and falls on the apertured mirror 3. The light is then reflected leftward by a mirror portion in the periphery of the apertured mirror 3, passes through the objective lens 1, and illuminates the fundus Er through the pupil Ep.

An image of the illuminated fundus Er passes through the objective lens 1, the photographing aperture 2, the focus lens 4, and the photographing lens 5, is reflected by the quick return mirror 6, and brought to the ocular lens 9. The photographer observes the fundus image of the subject's eye E through the ocular lens 9, and performs alignment of the fundus camera, confirmation of the place to be photographed, focusing by the focusing unit 16, and so forth.

Figure 3:
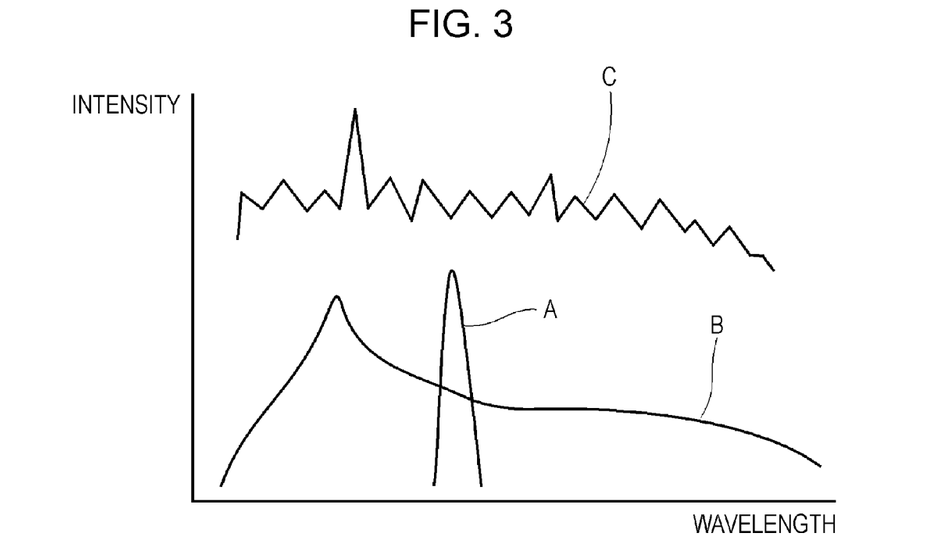
FIG. 3 is a graph of emission spectra of the light sources.

FIG. 3 is a graph showing wavelength vs. emission intensity of characteristic A of the index illuminating member 15, which is a green LED, of the focusing unit 16, characteristic B of white LEDs 22a to 22f of the observation illuminating member 22, and characteristic C of the photographing illuminating member 21. Since the photographer observes with the naked eye using the ocular lens 9, a green (visible light) LED is used in the index illuminating member 15 of the focusing unit 16. In consideration of color photographing of a fundus image and color reproduction in observation, a continuous white spectrum is used in photographing light beams of the photographing illuminating member 21 and observation light beams of the observation illuminating member 22.

Figure 4:
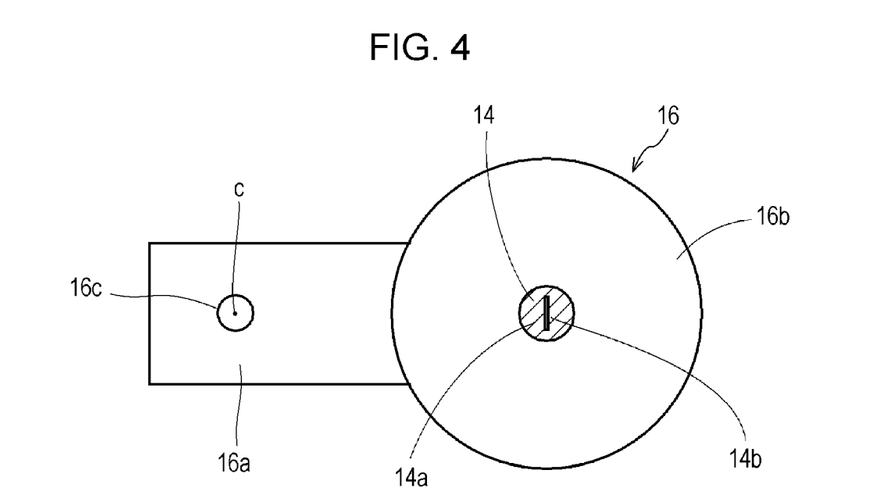
FIG. 4 is a plan view of a focusing unit.
Figure 5:
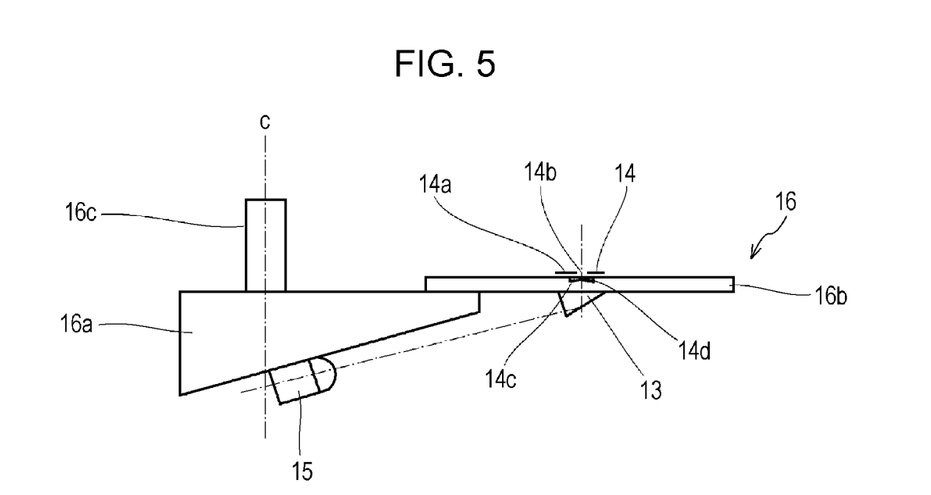
FIG. 5 is a side view of the focusing unit.
Figure 6:
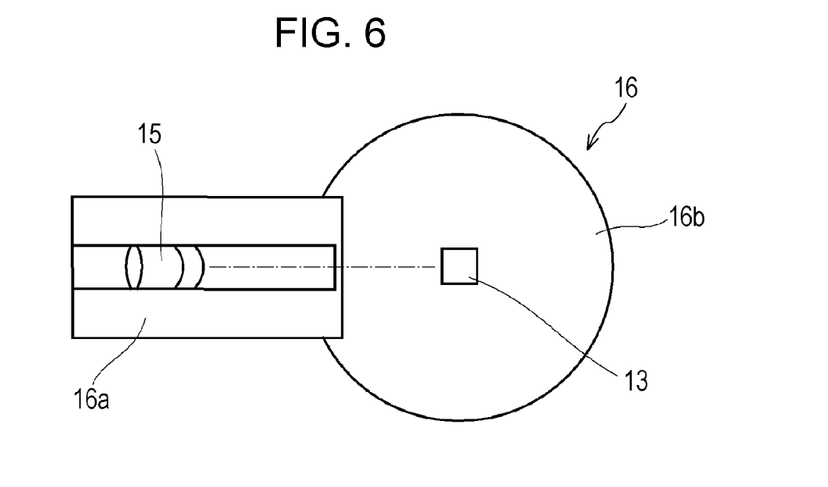
FIG. 6 is a bottom view of the focusing unit.

FIGS. 4 to 6 are plan view, side view, and bottom view, respectively, of the focusing unit 16. The index illuminating member 15, which is a green LED, is attached to the bottom of a base 16a. A transparent disk 16b formed, for example, of acrylic resin is fixed to the base 16a. The deflection prism 13 is attached to the bottom of the disk 16b so that a light beam from the index illuminating member 15 enters the deflection prism 13. The focus index forming portion 14 is provided on the top of the disk 16b. The focus index forming portion 14 includes a slit-like opening 14b provided in the center of a light-shielding portion 14a. A pair of split prisms 14c and 14d are provided under the opening 14b.

Figure 7:
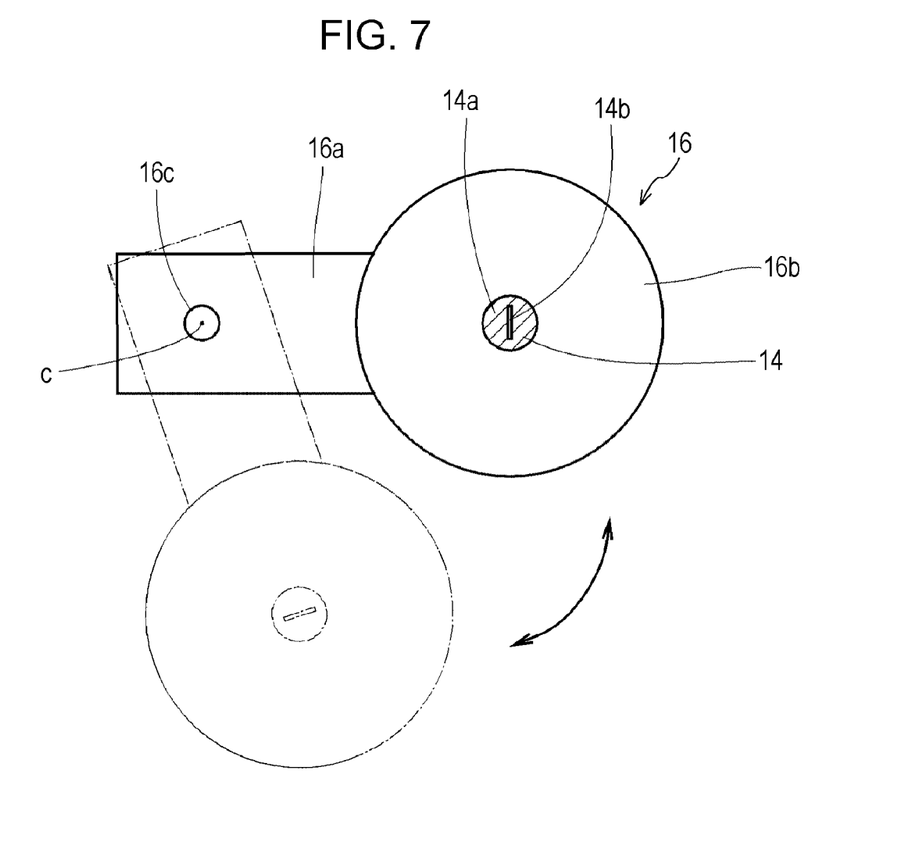
FIG. 7 illustrates the movement of the focusing unit.

The focusing unit 16 has a supporting portion 16c for rotating around a rotation axis c. By rotating around the rotation axis c as shown in FIG. 7, the focusing unit 16 can be inserted into and removed from the light path of the illumination optical system.

Figure 8:
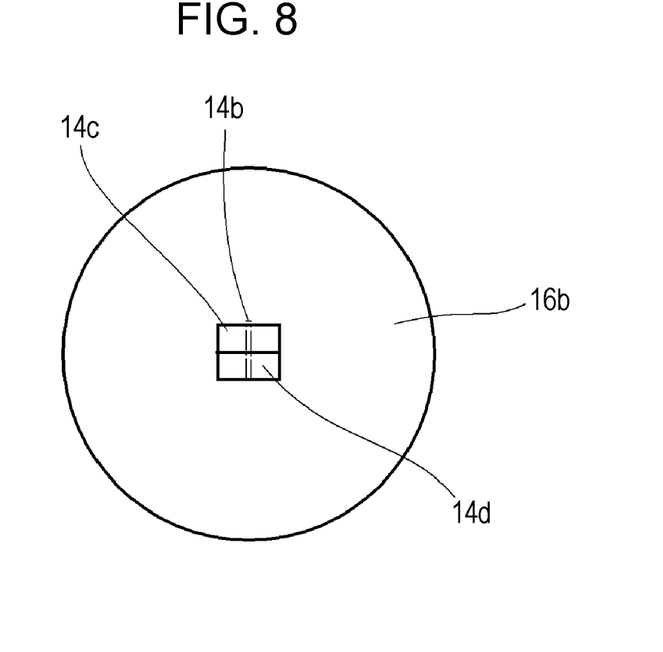
FIG. 8 illustrates a spilt prism.

As shown in FIG. 8, the split prisms 14c and 14d are a pair of prisms that divide the opening 14b in two. These prisms are attached so that their deflection directions are opposite to each other. Therefore, deflected by the prisms 14c and 14d, the light beam from the index illuminating member 15 is split into two, right-half and left-half, directional beams and combined with the illumination optical system in the form of two slit images at the diaphragm opening 14b.

Figure 9:
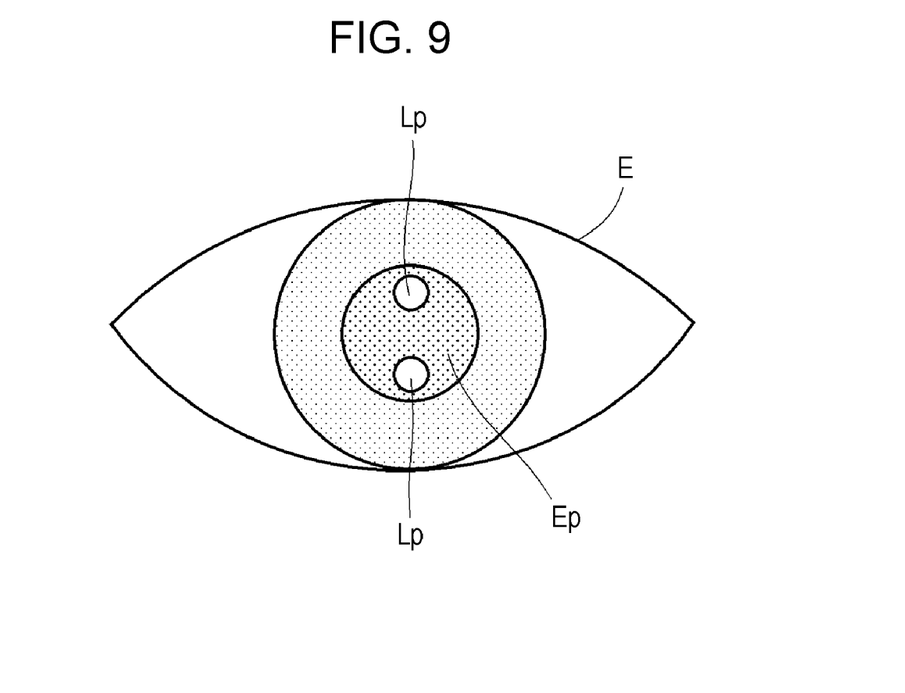
FIG. 9 illustrates an anterior eye image.

When the focusing unit 16 is inserted into the illumination optical system as shown in FIG. 1, the focus index forming portion 14 is located in the center of the illumination light path, and two light beams from the slit opening 14b are projected onto the pupil Ep of the subject's eye E, in the form of bright points, together with illuminating light from the observation illuminating member 22. Thus, the two bright points Lp occupy the positions shown in FIG. 9 in an anterior eye image. The movement of the focus lens 4 does not significantly change these positions.

Figure 10A:
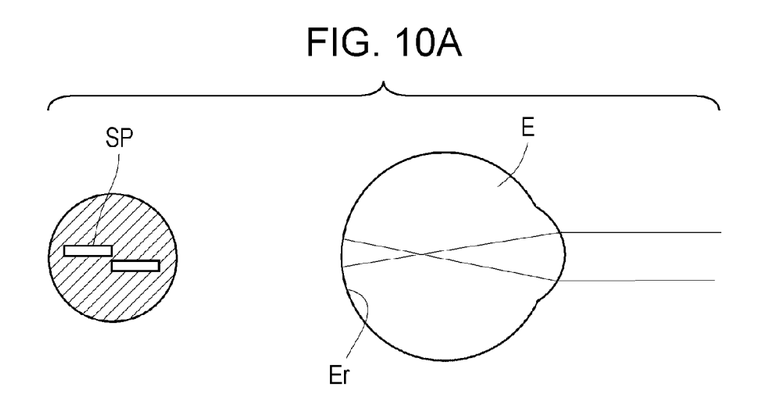
FIGS. 10A to 10C illustrate separation of slit images at a fundus.
Figure 10B:
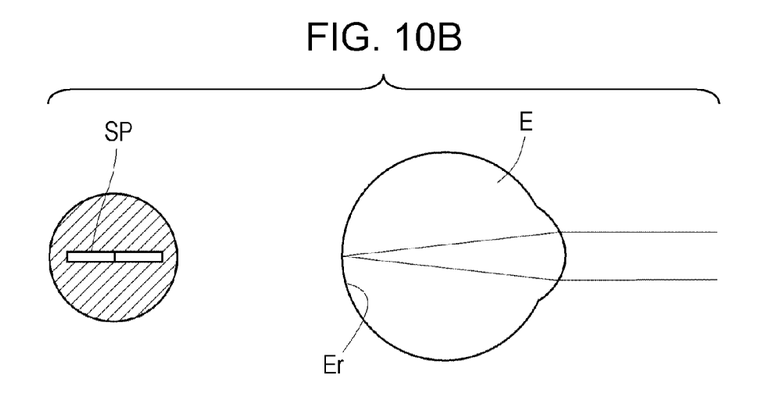
Figure 10C:
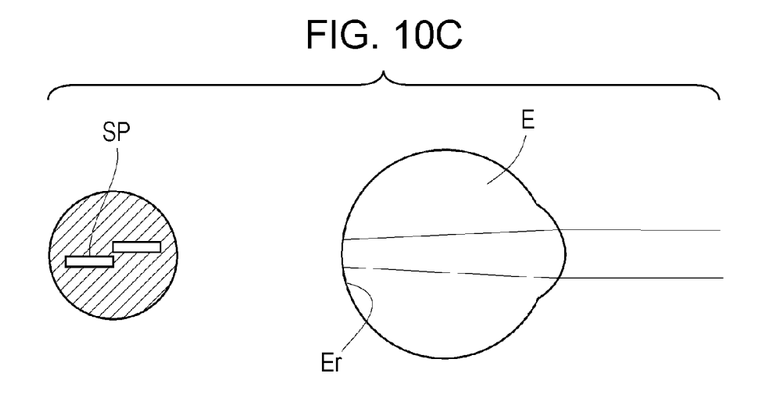

The two light beams projected from the bright points Lp form slit images on the fundus Er. In FIGS. 10A and 10C, the projection positions of the slit images SP are not aligned with the fundus Er, the projected right and left slit images SP being vertically separated. In contrast, when the projection positions of the slit images SP are aligned with the fundus Er as shown in FIG. 10B, the right and left slit images SP are aligned.

The slit images SP projected onto the fundus Er pass through the pupil Ep, the objective lens 1, the photographing aperture 2, the focus lens 4, and the photographing lens 5, are reflected by the quick return mirror 6, and brought to the ocular lens 9. The photographer moves the focus lens 4 so that these slit images SP are aligned. In conjunction with this, the focusing unit 16 moves in the optical axis direction. Since the focus lens 4 is adjusted so that the image pickup surface is always conjugate with the projection surface of the focus index forming portion 14, an in-focus image can be obtained by photographing with the slit images SP aligned. Thus, the slit images SP projected through the split prisms 14c and 14d function as indices showing the focusing state in fundus photography.

After alignment is completed by performing the above operation, the photographer presses the photographing switch 24. Detecting the input of the photographing switch 24, the control unit 23 turns off the white LEDs 22a to 22f with the light source driving circuit 27, removes the focusing unit 16 from the light path with the focusing unit driving unit 28, and also removes the quick return mirror 6 from the light path.

The control unit 23 orders the light source driving circuit 27 to make the photographing illuminating member 21 instantaneously emit light. The light beams emitted from the photographing illuminating member 21 pass through the opening of the diaphragm 20 and the opening of the diaphragm 19 and fall on the mirror 18. The light reflected upward by this mirror 18 passes through the relay lens 17, the black dot plate 12, the relay lens 11, and the opening of the diaphragm 10, is reflected leftward by the mirror portion of the apertured mirror 3, and illuminates the fundus Er through the objective lens 1 and the pupil Ep. After illuminating the fundus, the light passes through the pupil Ep, the objective lens 1, the photographing aperture 2, the focus lens 4, and the photographing lens 5 and forms an image of the fundus on the image pickup element 7. The fundus image is converted into an electric signal in the image pickup element 7, imported into the control unit 23, and thereafter displayed on the monitor 26 and recorded in the storage unit 25.

After this series of photographing operations are completed, the control unit 23 moves the focusing unit 16 into the light path once again, turns on the white LEDs 22a to 22f, and goes into standby mode.

Figure 11A:
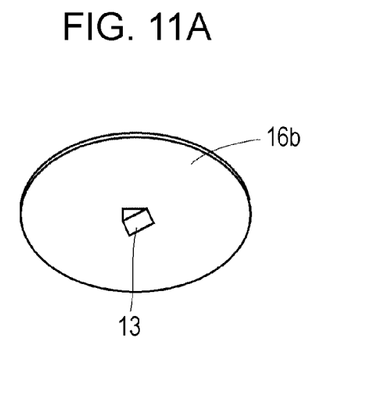
FIGS. 11A and 11B are perspective views of a modification of the focusing unit.
Figure 11B:
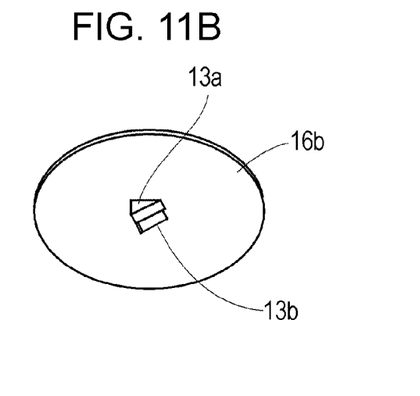

FIGS. 11A and 11B are perspective views of the underside of disk 16b of the focusing unit 16. FIG. 11A shows the above-described deflection prism 13 of the focusing unit 16. FIG. 11B shows a modification thereof, which includes deflection prisms 13a and 13b having two differently angled reflecting surfaces. These deflection prisms 13a and 13b have the same function as the split prisms 14c and 14d. Using such deflection prisms 13a and 13b makes the split prisms 14c and 14d unnecessary and makes it possible to form the opening 14b in the disk 16b using the technique of silkscreen printing or the like.

Figure 12:
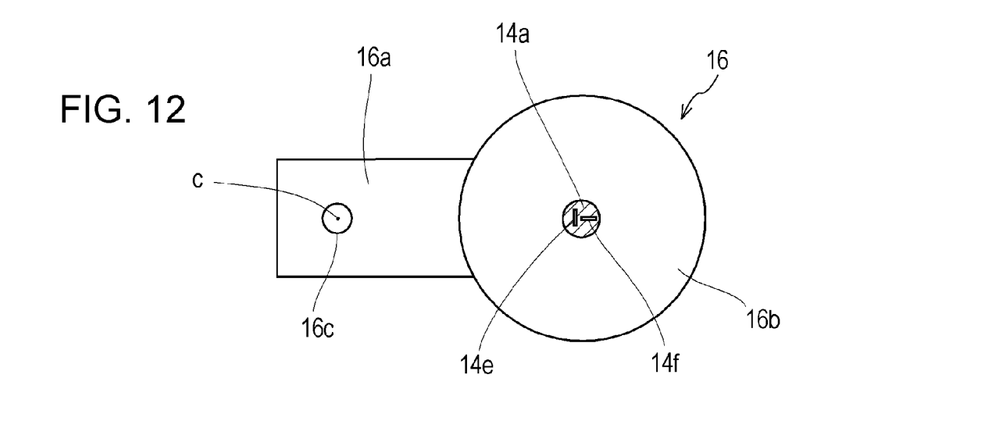
FIG. 12 is a plan view of another modification of the focusing unit.
Figure 13:
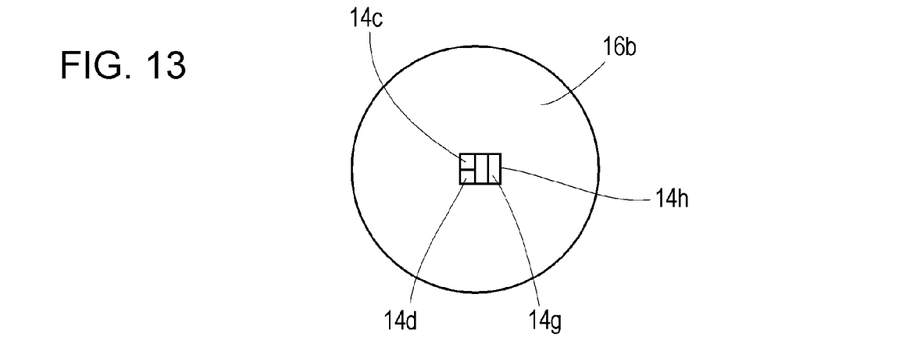
FIG. 13 illustrates a spilt prism.

FIGS. 12 and 13 show another modification of the focusing unit 16. Two mutually-perpendicular openings 14e and 14f are provided in the light-shielding portion 14a of the focus index forming portion 14. Split prisms 14g and 14h are disposed under the openings 14e and 14f together with the split prisms 14c and 14d shown in FIG. 8. Although the direction of inclination of the split prisms 14c and 14d is the same as in FIG. 8, the inclination of the split prisms 14g and 14h is perpendicular to the split prisms 14c and 14d.

Thus, light beams from the openings 14e and 14f projected onto the fundus Er are split into four slit images, and it becomes possible to perform two-meridian focusing in consideration of a case where the subject's eye E has astigmatism, and astigmatism occurring when the periphery of the fundus Er is photographed.

The focusing unit according to the present invention can make it possible to downsize ophthalmic photographing apparatuses without generating ghost light. The ophthalmic photographing apparatus according to the present invention can be downsized without emitting ghost light.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-321633 filed Nov. 29, 2006, which is hereby incorporated by reference herein in its entirety.

What is claimed is:

1. An ophthalmic photographing apparatus comprising:
   an illumination optical unit having a first illuminating member for illuminating a subject's eye;
   a crystalline lens diaphragm that adjusts a range of a crystalline lens of the subject's eye where the light emitted by the first illuminating member illuminates, wherein the crystalline lens diaphragm has a ring-shaped opening;
   a focusing lens that adjusts a focal point;
   a photographing optical system including an image sensor that converts an optical image that enters via the focus lens into an electrical signal;
   a first unit including an index illumination optical unit, a first opening that forms a focus index, and a split prism disposed near the opening being integrated; and
   a driving unit that moves the first unit in a direction of the optical axis of the illuminating member together with the movement of the focus lens,
   wherein when the first opening is positioned in an optical axis of the first illuminating member, the index illumination optical unit has an optical axis different from that of the first illuminating member.

2. The ophthalmic photographing apparatus according to claim 1, further comprising a second opening that forms a second focus index, and a second split prism disposed near the opening being integrated, wherein the first opening and the second opening have opposite directions to each other.

3. The ophthalmic photographing apparatus according to claim 1, wherein the first unit can be inserted into and removed from the light path of the illumination optical unit.

* * * * *